(12) United States Patent
McKirdy et al.

(10) Patent No.: US 11,252,235 B2
(45) Date of Patent: Feb. 15, 2022

(54) SYSTEM AND METHOD FOR PROCESSING INFORMATION

(71) Applicant: Fitistics, LLC, Newington, CT (US)

(72) Inventors: Sean McKirdy, Newington, CT (US); Robert Nutini, Suffield, CT (US)

( * ) Notice: Subject to any disclaimer, the term of this patent is extended or adjusted under 35 U.S.C. 154(b) by 0 days.

(21) Appl. No.: 16/570,424

(22) Filed: Sep. 13, 2019

(65) Prior Publication Data

US 2020/0007626 A1 Jan. 2, 2020

Related U.S. Application Data

(63) Continuation of application No. 15/809,174, filed on Nov. 10, 2017, and a continuation of application No. 14/203,648, filed on Mar. 11, 2014.

(51) Int. Cl.
| | |
|---|---|
| *A61B 5/00* | (2006.01) |
| *A61B 5/0205* | (2006.01) |
| *H04L 67/12* | (2022.01) |
| *H04L 67/50* | (2022.01) |
| *G16H 40/67* | (2018.01) |
| *G16H 20/30* | (2018.01) |
| *A63B 24/00* | (2006.01) |
| *A63B 71/06* | (2006.01) |
| *G16H 50/30* | (2018.01) |
| *G16H 50/20* | (2018.01) |

(52) U.S. Cl.
CPC ............ *H04L 67/12* (2013.01); *A61B 5/0002* (2013.01); *A61B 5/0205* (2013.01); *A63B 24/0075* (2013.01); *A63B 71/0622* (2013.01); *G16H 20/30* (2018.01); *G16H 40/67* (2018.01); *H04L 67/22* (2013.01); *A61B 5/4833* (2013.01); *A61B 5/4839* (2013.01); *A63B 2225/50* (2013.01); *G16H 50/20* (2018.01); *G16H 50/30* (2018.01)

(58) Field of Classification Search
CPC . A63B 24/0075; A63B 71/0622; H04L 67/12; H04L 67/22; G09B 19/003; G09B 19/0092; G09B 19/0038; G16H 20/30; G16H 40/67; A61B 5/0002; A61B 5/0205
See application file for complete search history.

(56) References Cited

U.S. PATENT DOCUMENTS

| | | | | |
|---|---|---|---|---|
| 6,513,532 | B2 * | 2/2003 | Mault ................ | G01N 33/497 600/595 |
| 2002/0013717 | A1 * | 1/2002 | Ando ................... | G16H 20/30 705/4 |

(Continued)

*Primary Examiner* — Malina D. Blaise
(74) *Attorney, Agent, or Firm* — Steven M. McHugh

(57) ABSTRACT

A system for processing biological data is provided and includes a monitoring device configured to receive biological data responsive to a living being. The system also includes an interface device communicated with the monitoring device to receive the biological data. Furthermore, the system includes a data transfer device, configured to receive the biological data from the interface device and communicate the biological data to a processing device for processing. Additionally, a method for processing biological information is provided, wherein the method includes receiving biological information from a monitoring device responsive to a first party and responsive to an exercise regime and processing the biological information to generate resultant information responsive to at least one physical characteristic of the first party.

22 Claims, 8 Drawing Sheets

(56) References Cited

U.S. PATENT DOCUMENTS

| | | | |
|---|---|---|---|
| 2002/0123325 A1* | 9/2002 | Cooper | H04W 12/50 455/411 |
| 2006/0122474 A1* | 6/2006 | Teller | G16H 15/00 600/300 |
| 2007/0219059 A1* | 9/2007 | Schwartz | A61B 7/003 482/8 |
| 2008/0109158 A1* | 5/2008 | Huhtala | A63B 24/0084 701/439 |
| 2008/0139907 A1* | 6/2008 | Rao | A61B 5/1171 600/323 |

* cited by examiner

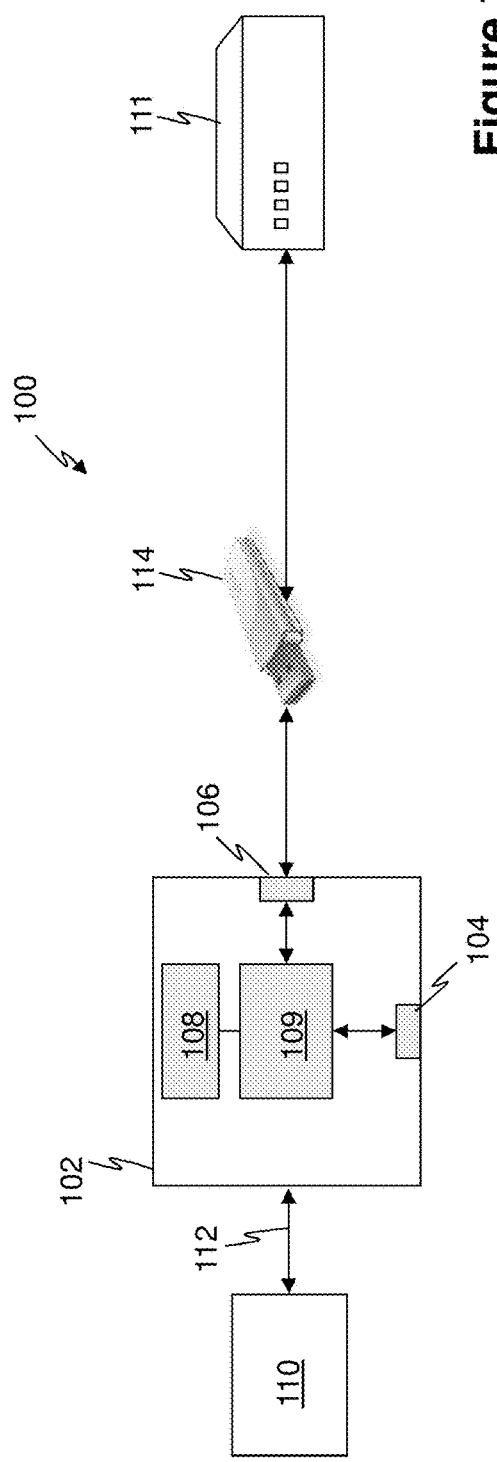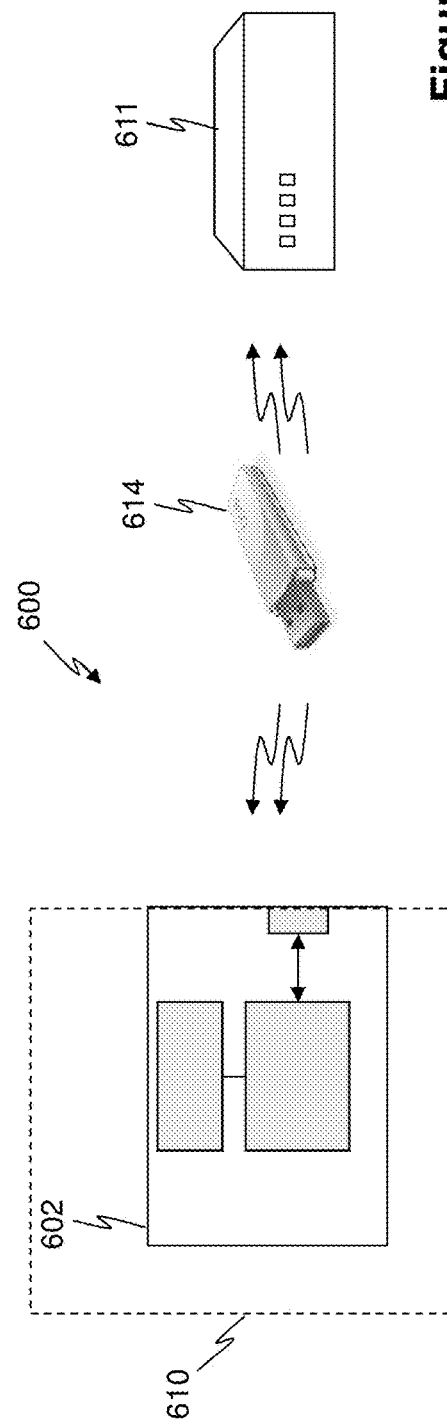

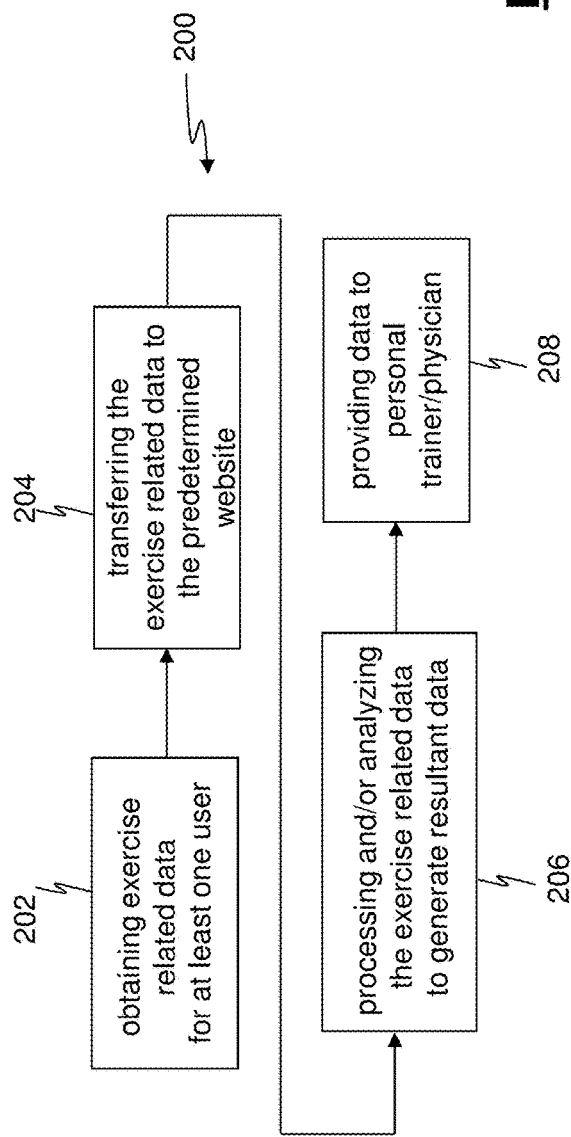
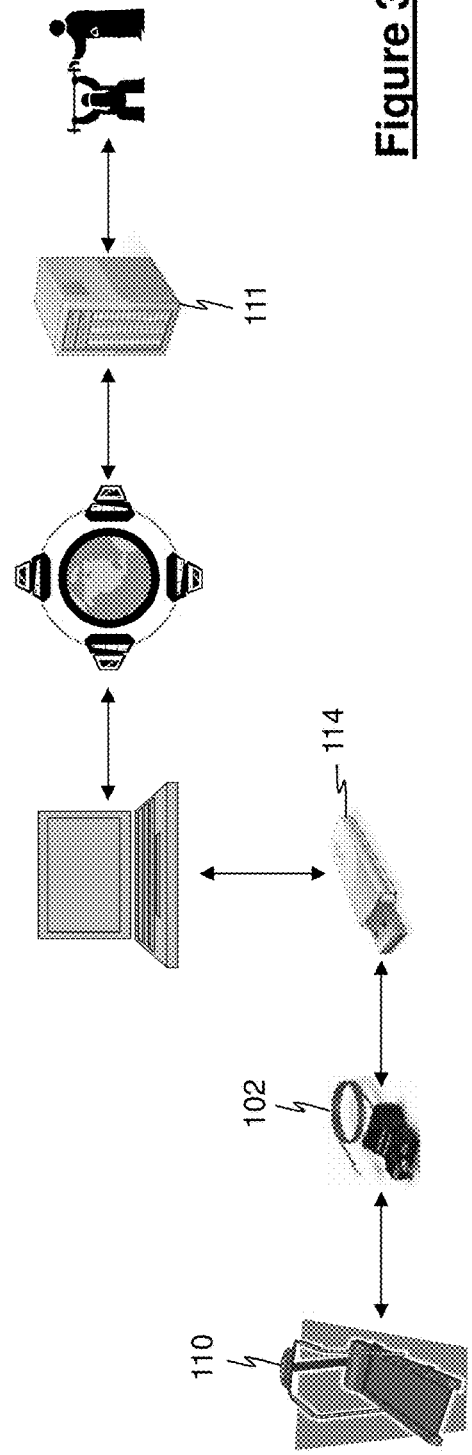

SYSTEM AND METHOD FOR PROCESSING INFORMATION

CROSS-REFERENCE TO RELATED PATENT APPLICATIONS

The present application is a continuation application of U.S. Non-Provisional patent application Ser. No. 15/809,174 filed Nov. 10, 2017 and claims the benefit of priority of the filing date of U.S. Non-Provisional patent application Ser. No. 15/809,174 filed Nov. 10, 2017 and U.S. Non-Provisional patent application Ser. No. 14/203,648 and is related to U.S. Non-Provisional patent application Ser. No. 11/998,766 and U.S. Provisional Patent Application Ser. No. 60/872,203, filed on Dec. 1, 2006 the contents of all of which are incorporated by reference herein in their entirety.

FIELD OF THE INVENTION

This disclosure relates generally to the processing of information and more particularly to a system and method for obtaining, processing and implementing exercise related information.

BACKGROUND OF THE INVENTION

For many years, people have recognized the health benefits of exercising on a regular basis. As a result, a whole industry dedicated to physical fitness and exercise was created and has grown into a multi-billion dollar a year industry. Areas of this industry, which includes personal trainers, fitness clubs, nutrition based products, exercise gear and fitness competitions, tend to complement each other and work hand in hand with each other to help individuals achieve an effective physical fitness regimen. For example, a large number of fitness clubs employ nutritionists and personal trainers that are readily available to advise their fitness club members, wherein the basic services that these personal trainers perform are primarily three fold. First, the trainers develop an exercise regime tailored to individual clients and advise their clients on how to safely and effectively exercise. Second, the trainers track the exercise performance of the client over the duration of the training period and analyze the client's exercise performance data to identify where the client is or is not showing improvements. The trainer may then adjust the exercise regime of the client to maximize the benefit to the client. Third, the trainer provides motivation to their client, which ultimately helps the client to maintain their exercise regime. This not only aids the client in maintaining a healthy lifestyle, but also helps the fitness club retain their membership.

Unfortunately however, because personal trainers are expensive to employ, most fitness clubs only have one or two trainers on staff to assist hundreds of members and as such, the on-staff trainers are typically not able to spend a significant amount of time with each individual member. Accordingly, in order for the member to obtain the full benefit of their club membership, the member must hire the trainer outside of their health club membership or they must analyze their performance and adjust their exercise regime using other methods. While there are systems currently available that provide some data tracking services and motivational tools for exercise, these systems include several undesirable characteristics. One such characteristic involves the availability and cost of the system. For example, current systems are not readily available to the majority of commercial gyms or to the individual because they are expensive and require a high capital investment. Another such characteristic involves the compatibility between the existing systems and the exercise equipment. For example, the ability of the existing systems to connect to a typical workout machine is limited due to communication and functional issues between the tracking system and the exercise machine, as well as due to the layout of the fitness club. Still yet another undesirable characteristic involves the lack of functionality of the existing systems and its ease of use. For example, one such system employs a computerized kiosk that requires the user of the exercise equipment to manually input their work out data. Whereas another such system employs the use of an electronic key that can only interact with a specific line of exercise equipment. Thus, if the user were to use exercise equipment that was not able to interface with the electronic key, the user would need to input their exercise data manually using a computerized kiosk.

Unfortunately, all of the existing systems require the user of the exercise equipment to either use some unique device to interface with a specific machine or to manually interact with a stand-alone computer terminal where the data being entered is prone to data entry errors and/or misuse.

SUMMARY OF THE INVENTION

A system for processing biological data is provided and includes a monitoring device configured to receive biological data responsive to a living being. The system also includes an interface device communicated with the monitoring device to receive the biological data. Furthermore, the system includes a data transfer device, configured to receive the biological data from the interface device and communicate the biological data to a processing device for processing.

An interface device for facilitating communication of biological data between a monitoring device and a data transfer device is provided, wherein the interface device includes a first communication port configured to communicate the interface device with the monitoring device to allow the transfer of data there between. Additionally, the interface device includes a second communication port configured to communicate the interface device with the data transfer device to allow the transfer of data there between. Furthermore, the interface device includes a processing device in electrical communication with the first communication port and the second communication port, wherein the processing device is configured to facilitate transfer of data between the first communication port and the second communication port.

A method for processing biological information is provided, wherein the method includes receiving biological information from a monitoring device responsive to a first party and responsive to an exercise regime and processing the biological information to generate resultant information responsive to at least one physical characteristic of the first party.

BRIEF DESCRIPTION OF DRAWINGS

The foregoing and other features and advantages of the present invention will be better understood from the following detailed description of illustrative embodiments, taken in conjunction with the accompanying drawings in which:

FIG. 1A illustrates one embodiment of a system for processing exercise information, in accordance with the present invention

FIG. 1F illustrates a second embodiment of the present invention, wherein the docking station is integrated with an exercise device.

FIG. 2 is a block diagram illustrating a first embodiment of the method of the present invention;

FIG. 3 is a block diagram illustrating the interaction of the system of FIG. 1, in accordance with the method of FIG. 2;

DETAILED DESCRIPTION OF THE INVENTION

Figure 1B:
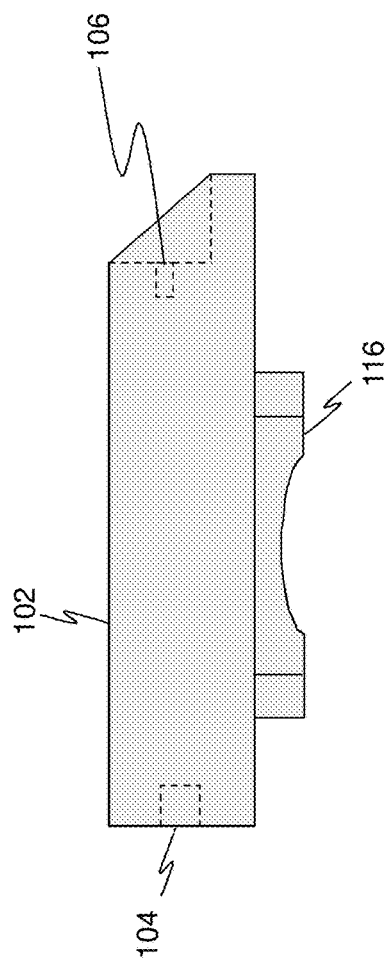
FIG. 1B illustrates a side view of one embodiment of the docking station in FIG. 1, in accordance with the present invention.

In accordance with the present invention, a system and method for processing information is discussed herein as being applied to exercise and/or health related information. However, it should be appreciated that the present invention may also be applied to other types of information as well, including educational progress information, financial progress information and any other type of information suitable to the desired end purpose. As discussed in further detail hereinafter, the present invention allows exercise information to be accurately obtained, stored and processed by providing an affordable data tracking system that offers universal connectivity to common exercise machines that allow for data generation and transfer, such as exercise machines that implement CSAFE data transfer protocols. The present invention also enables the accurate and efficient transfer of exercise information by allowing the user of the exercise machine to use common storage devices, such as a USB flash drive device, to capture their personal workout data which can then be uploaded to a database driven website using minimal user interaction. Furthermore, the present invention allows for the efficient processing and display of the data in a user-friendly format (graphical or non-graphical), thus allowing a user or personal trainer to track and compare the workout data with the statistics of other users. Additionally, the present invention is also capable of offering virtual online competitions, such as races or weight lifting, where a plurality of users can submit their best performance data for a competition event, making them eligible for rewards in the form of points, prizes, or coupons from website sponsors.

Referring to FIG. 1A, one embodiment of a system 100 for processing exercise information in accordance with the present invention is illustrated. The system 100 includes an interface device or docking station 102 having a machine interface port 104 and a user interface port 106 communicated with a docking station storage device 108, wherein the machine interface port 104 is an shown as an RJ45 serial communications port and the user interface port 106 is shown as a USB port. The docking station 102 is in signal communication with an exercise device (or monitoring device) 110 via a serial communication link 112 between the machine interface port 104 and the exercise device 110. Accordingly, when exercise data is generated by the user interacting with the exercise device 110, the exercise data may be transferred to the docking station 102 via the serial communication link 112. This exercise data may then be stored as discussed further hereinafter, at least temporarily, in the docking station storage device 108. It is contemplated that the docking station storage device 108 may be any type of storage device suitable to the desired end purpose, such as RAM and/or a flash storage device that is disposed internal and/or external to the docking station 102.

Additionally, the user interface port 106 may be a USB port to allow the user to easily transfer the exercise data stored by the docking station storage device 108 to a portable USB flash drive 114. It should be appreciated that although information transfer is discussed hereinabove with regards to information being transferred from the exercise device 110 to the portable USB flash drive 114 via the docking station 102, it is contemplated that information may also be transferred in the opposite direction, i.e. from the USB flash drive 114 to the exercise device 110 via the docking station 102. And as such, the USB flash drive 114 may be used to program characteristics of the exercise device 110, such as functionality and display.

Accordingly, the present invention advantageously allows information to be transferred between the docking station 102 and the exercise device 110. Furthermore, although the docking station 102 is disclosed herein as being connected with the exercise device 110 via a wired serial communication link 112, it is contemplated that the docking station 102 may be communicated with the exercise device 110 via any method suitable to the desired end purpose, such as a wireless communication link. Similarly, although the docking station 102 is disclosed herein as being connectable to the portable USB flash drive 114 via user interface port 106, the docking station 102 may also be communicated with the portable USB flash drive 114 via any method suitable to the desired end purpose, such as a wireless communication link using any technology suitable to the desired end purpose, including but not limited to Bluetooth, RFID, Infrared, Microwave, RF and Cellular technology. Additionally, at least one of the docking station 102 and the exercise device 110 may include software that conforms to a desired communications protocol for transferring information, such as user biological data, exercise performance data and/or exercise device data, between the exercise device 110 and the docking station 102.

For example, in accordance with the present invention the docking station 102 may include a processing device 109, such as a microprocessor or microcontroller, and appropriate software/commands, such as embedded CSAFE commands, working in conjunction with software/firmware and drivers residing on the processing device that has the ability to communicate with a variety of exercise devices 110, such as, but not limited to commercial/residential quality exercise and cardio fitness machines; retrofit hardware devices used with exercise equipment (including, but not limited to, road bicycles, rowing machines, mountain bikes, 'spin class' bikes); strength training equipment fitted with electro-mechanical devices capable of translating the act of using free weights and other strength machines into electronic data; and existing fitness tracking hardware and/or software.

It should be appreciated that any and all communications discussed hereinabove to the docking station 102 may be made via any connection (and/or information transfer) device and/or method suitable to the desired end purpose, such as via wireless communications and/or serial RJ45/RS232 serial ports currently existing on CSAFE compatible machines. The system may also incorporate other communication protocols, including but not limited to USB port protocols, WI FI connection protocols, radio frequency (i.e. RFID, etc), microwave, infrared, fiber optic, and/or Blue Tooth protocols. As such, any communications protocol suitable to the desired end purpose may be used to transfer exercise data between the docking station 102 and the exercise device 110, such as via the CSAFE protocol.

Once the exercise data has been transferred to the docking station device 102, the user may then transfer the stored exercise data from the docking station device 102 to the portable, temporary storage device 114, i.e. the USB flash drive. This may be accomplished by inserting the USB flash drive 114 into the user interface port 106, wherein once the USB flash drive 114 is inserted into the user interface port 106, the exercise data may begin automatically (or manually) transferring between the docking station device 102 and the USB flash drive 114. It is contemplated that, although the invention is discussed herein in terms of transferring data between devices via a direct hardware interface, wireless communication interfaces may also be used as desired. It should be appreciated that the exercise data may be encrypted using software encryption algorithm (s) to prevent a user from fraudulently manipulating their exercise data. Additionally, bio-metric security devices (as well as other types of security devices/methods, such as USB fingerprint flash drives) may also be used to further enhance and protect the integrity of the exercise data and/or system functionality. This capability allows for proof of exercise with a high level of integrity and confidence.

Once the user has completed their exercise regime, the user would transfer or upload their exercise data from the USB flash drive 114 to a processing hub 111, such as a predetermined website maintained and operated by an administrator. The predetermined website may then process and/or analyze the exercise data so that the exercise data can be viewed in a desired format, such as a graphical manner and/or a tabular format. This upload may be accomplished by the user inserting the USB flash drive 114 containing the exercise data into the USB port on their computer (standard on most computers) and uploading the exercise data to the predetermined website. This upload may be manually implemented by the user or automatically implemented via software installed on the USB flash drive 114 or via software installed on the user's computer. Once the exercise data is uploaded to the predetermined website, the exercise data may also be processed and/or analyzed in order to implement the method of the invention as discussed further hereinafter.

It is contemplated that the website administrator would offer services to a user to enable the user to view their individual performance trends, compare their statistics to other members and compete with other members via virtual competitions, such as biking, running, rowing, elliptical, and other races where winners may be rewarded. For example, the user may connect the USB flash drive 114 containing the exercise data to a data transfer device or computing device 109 having an internet connection. As discussed herein, an executable program may be included on the computing device 109 (or USB flash drive 114) which may automatically cause all or some specific files from the USB flash drive 114 to transfer to an online database associated with the website hosted by the supervising body. All or some of the data may then be displayed to the user in a desired format, i.e. graphical, tabular, etc. In one embodiment, it is contemplated that the exercise data that is uploaded to the website may be erased from the USB flash drive 114 using a software program (or other method/device) designed to erase workout files as the files are uploaded to prevent the flash drive from storing old exercise data. This would help to maintain the integrity of the exercise data by allowing the activity on the USB flash drive 114 to be tracked. Additionally, the website may include a unique virtual online competition section that registered users can use to compete against each other. This competitive section of the website may be specific to certain groups, such as the type of machine (treadmill, stationary bike, spin bike, elliptical machine, cross trainer, rower, etc), age of person, size of person, physical attributes of person, sex of person, health status of person, etc. Moreover, the competitive section may include online competitive events, such as online racing events that the users may pre-register for, wherein top place finishers in competitions may receive prizes and rewards.

The website may also provide the services of health, dietary and exercise professionals for consultations to further help the user meet their fitness and health goals. Additionally, the website may provide motivation to the user to continue exercising through the use of data tracking, competition, rewards, health care benefits, dietary information, and community membership. Accordingly, the present invention advantageously allows a user to capture exercise data, such as workout statistics, biological information, machine performance information, etc, from a plurality of exercise devices 110 and store this data onto one convenient memory device for later processing and/or analysis. It should be appreciated that the present invention allows other information to be extracted as well, including but not limited to, machine make and model, machine performance information (measurement accuracy, calibration, etc.) speed, time elapsed during workout, preset program used, date, calories burned, heart rate, distance, elevation, body fat % of user, and age/weight of user. For example, one example of information that may be extracted and communicated to the website may include:

Example: LifeFitness, 93Ci, 5 mph, 34 minutes, Speed training, 10-16-06, 2500 cal, 120 bpm, 4 miles, n/a, 12%, 45/185 lbs.

Accordingly, the website may allow for the comparison of data across multiple different exercise devices 110 and may show registered users which exercise devices 110 provide them with the best results. Furthermore, the website may automatically email the registered user with updates on their weekly, monthly, quarterly, and/or yearly progress. This feedback may include results or status of race events that users have entered into as well as information on financial savings on health products and services to which they have asked to be kept aware. Additionally, the exercise data may be scanned to determine if the user has any health issues that the user may be unaware of and if so, may inform the user of such results. The website may post local and national rankings for users based on a predetermined characteristic, such as may be determined by profile information of registered users in one club or in many different clubs. Thus, the website would show the users how they compare to other members of their fitness clubs as well as members of other clubs using the system. This information may provide another motivational tool for the user to continue exercising. One example of such information being displayed may include:

Example: Leader boards for most calories burned, miles run, steps climbed, fastest mile, in a week, month, year, etc Accordingly, in accordance with the present invention the website may offer dietary advice and tools that allow users to input and track their daily, weekly and monthly diets and receive recommended diet plans to help them reach their personal fitness and health goals. Basic wellness information may also be provided by the website as well as an in depth wellness analysis of the users physical conditioning depending on the amount of dietary input the users contribute. Additionally, the invention may provide the user with the latest information on certain topics based upon predetermined criteria. For example, a heart patient may receive the latest information on research and/or heart healthy exercises and foods. Moreover, the invention may provide a forum section that will enable people to discuss their personal opinions on fitness equipment and industry trends, exercise techniques, diet plans, etc. Additionally, a peer-to-peer meeting section may be provided to allow people to find others in their local or state area who share similar interests, such as physical fitness and healthy life style. As such, the invention may create an online community of users who share a common interest (working toward a healthy lifestyle) and provide an excellent platform for those people to meet and form relationships with one another.

Figure 1C:
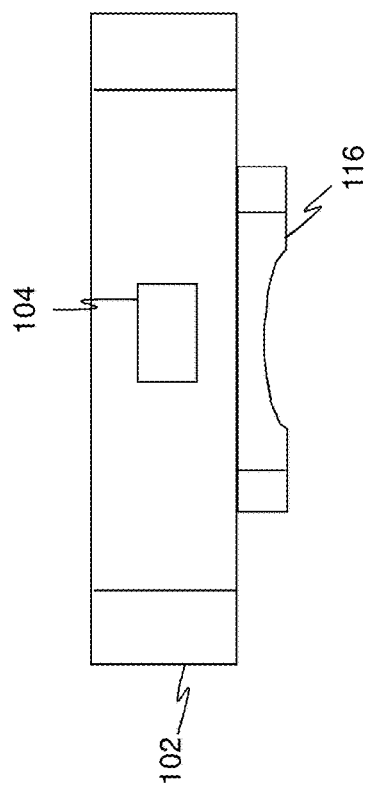
FIG. 1C illustrates a rear view of one embodiment of a docking station in FIG. 1.
Figure 1D:
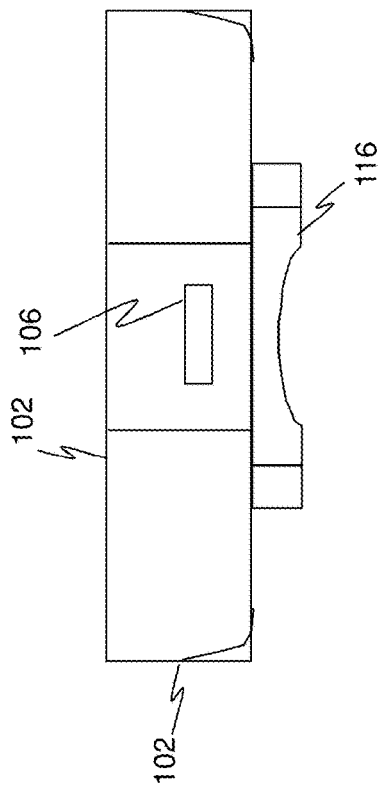
FIG. 1D illustrates a front view of one embodiment of a docking station in FIG. 1, in accordance with the present invention.
Figure 1E:
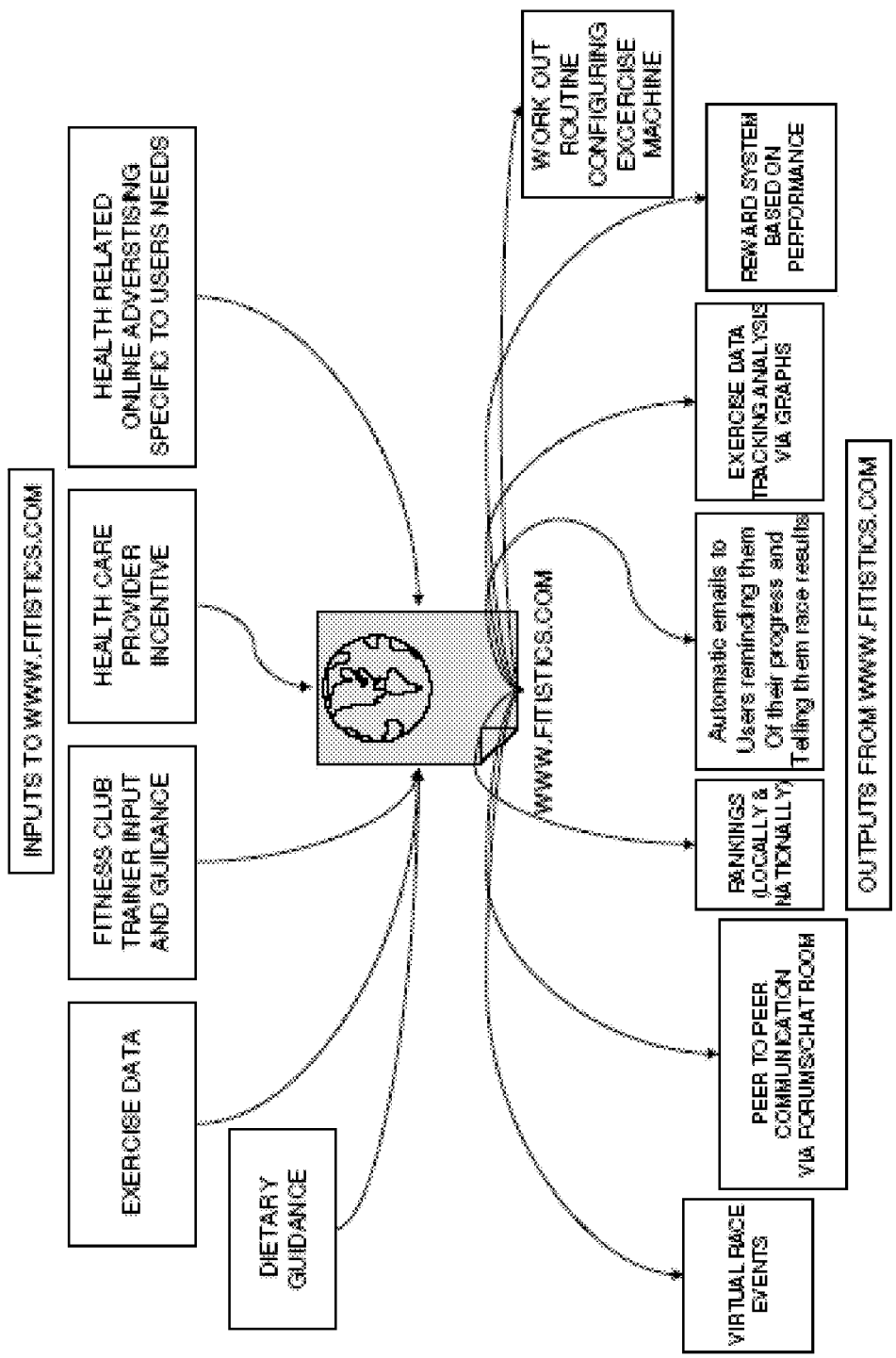
FIG. 1E is a block diagram illustrating one embodiment of the overall capability of the system of FIG. 1, in accordance with the present invention.

In accordance with the present invention, FIGS. 1B, 1C and 1D illustrate one embodiment of a docking station 100 and FIG. 1E illustrates an overall capability of the invention. As can be seen, docking station 100 may include a mounting portion 116 configure to securely associate with an exercise device 110.

Referring to FIG. 1F, a second embodiment of a system 600 for processing exercise information in accordance with the present invention is illustrated and is shown as a completely wireless system 600, but may be a partially wireless system. In this embodiment, the docking station 602 is shown as being integrated into the exercise device 610, but may be separate from the exercise device 610 as shown in embodiment 100. In this embodiment, the USB flash drive 614 may communicate wirelessly with both the exercise device 610 via integrated docking station 602 and the computing device 611 which may further communicate with the website either wirelessly or via a hardwired connection. Additionally, other configurations are contemplated as well, such as a system that as a user approaches the machine, the USB flash drive 614 and the exercise device 610 may automatically communicate and perhaps cause the exercise machine 610 to automatically get ready or configure itself for a particular user or exercise regime, which may be created by a user, a fitness or health care professional or other entity. If the user (or other entity) wants to create or modify an exercise regime, the system would include software to allow this function to be implemented. It is also contemplated that the exercise device 610 may communicate directly with the computing device 611 via wired or wireless connection, negating the need for use of the USB flash drive 614.

In accordance with the present invention, as disclosed herein the term exercise device is meant to include any type of device that generates, obtains and/or monitors biological information, such as a cardio-machine, an elliptical trainer, a heart rate monitor, a blood pressure monitor, etc. Accordingly, the present invention contemplates being used for any type of exercise such as biking, running and swimming, that does not use stationary fitness equipment. Additionally, the present invention contemplates being used for any living being, such as a pet that is under the care of a veterinarian. Furthermore, it is contemplated that some or all of the processing may be conducted by the computing device 109, 611 and/or by the interface device 102 prior to being communicated to the website for analysis or further processing.

Referring to FIG. 2, a block diagram illustrating a first embodiment of a method 200 for processing exercise related information is shown, wherein the method 200 includes obtaining exercise related data for at least one user, as shown in operational block 202. The exercise related data may then be transferred to the predetermined website, as shown in operational block 204. The exercise related data may then be processed and/or analyzed to generate resultant data, as shown in operational block 206. This resultant data may then be communicated to and used by a personal trainer and/or a physician to monitor and/or adjust the user's exercise performance, health status and/or exercise regime, as shown in operational block 208, as discussed further hereinafter. For example, the system may actively (continuous or semi-continuous monitoring) or passively (monitoring triggered by an event or threshold level) record a user's parameter (such as heart rate) through either embedded sensors on the exercise device 110 itself or through the user wearing a wireless monitor (such as a heart rate strap). This data may then be transferred and/or displayed over the duration (or limited desired period) of the workout, allowing the user to share this information with their primary care physician, cardiologist or other health professional. This information may be used to help treat the user, such as in the diagnosing of condition and/or prescribing of medications for diseases (for example, hypertension, diabetes, irregular heart beat, COPD, etc.). This information may also be used to help the user and/or user's personal trainer to better monitor their physical improvements, or lack of improvements over a desired period of time.

It should also be appreciated that operational block 202 and operational block 204 may be accomplished as described in greater detail hereinabove with regards to system 100. Alternatively, it is contemplated that other methods and/or devices for obtaining and transferring exercise related data to the predetermined website may also be used. Referring to FIG. 3, a block diagram illustrating one embodiment of the interconnectivity between the user, the exercise device 110 and the subject matter expert is shown.

In accordance with the present invention, this exercise related data and the resultant data may be used by a subject matter expert (such as a personal trainer, physical therapist and/or physician) to maximize the health benefit to the user as described hereinafter. Once the user has uploaded their exercise data from the USB flash drive 114 to the predetermined website, the exercise data might be processed and may be displayed along with the resultant data to the user in a desired format, such as a graphical and/or a tabular format. The raw exercise data and/or the resultant data may also be communicated to a subject matter expert who can then use this data to spot any potential health problems, develop a suitable exercise regime and/or adjust an existing exercise regime to help maximize the progress of the user. For example, if after reviewing the exercise data and the resultant data the subject matter expert wanted the exercise device 110 to have specific settings that are tailored to the user, the modified settings may be downloaded from the website onto the USB flash drive 114 for transfer to the exercise device 110 prior to the user working out. Accordingly, an exercise regime may be tailored or adjusted by the subject matter expert by allowing the subject matter expert to modify the settings of the exercise device 110 responsive to the raw exercise data and/or resultant data.

For example, consider the case where a user uploads their exercise data to the predetermined website from the USB flash drive 114. When the exercise data is processed and/or analyzed and reviewed by the subject matter expert it is noticed that the user is overstressing the heart muscle while exercising on a particular exercise device 110, such as the cardio device. The subject matter expert may then inform the user via the website that they are overstressing their heart muscle during this exercise. Additionally, the subject matter expert may also receive notification from the website of any irregularities or anomalies in the user's data that may indicate a health condition worth noting, such as an unknown irregular or abnormal heart rhythm or a user satisfying or not satisfying certain criteria for their prescribed exercise regime. This would allow for a quicker, more immediate opportunity for a doctor or trainer to address any potential problem. The subject matter expert may then advise the user to see their physician and/or download desired settings for the cardio device to the user's USB flash drive 114 to adjust the users exercise routine. The user would then be instructed to transfer these new device settings to the exercise device 110 via the USB flash drive 114 prior to exercising on the cardio device.

As an extension, the invention may enable a user to pre-load a complete or partial custom training program to the USB flash drive 114 and program the specific exercise devices they use during their exercise session. For example, a custom weekly/monthly fitness regimen may be pre-loaded onto the USB flash drive 114 and the user will follow that custom regimen on the corresponding machine types until the regime has been completed. This would advantageously allow a personal trainer to customize an entire or partial exercise regime and access the user's exercise data as desired to monitor the user's progress and offer guidance. This exercise data can also be used to provide feedback to health club facilities regarding which machines are the most popular and which machines offer the best workout.

Figure 4:
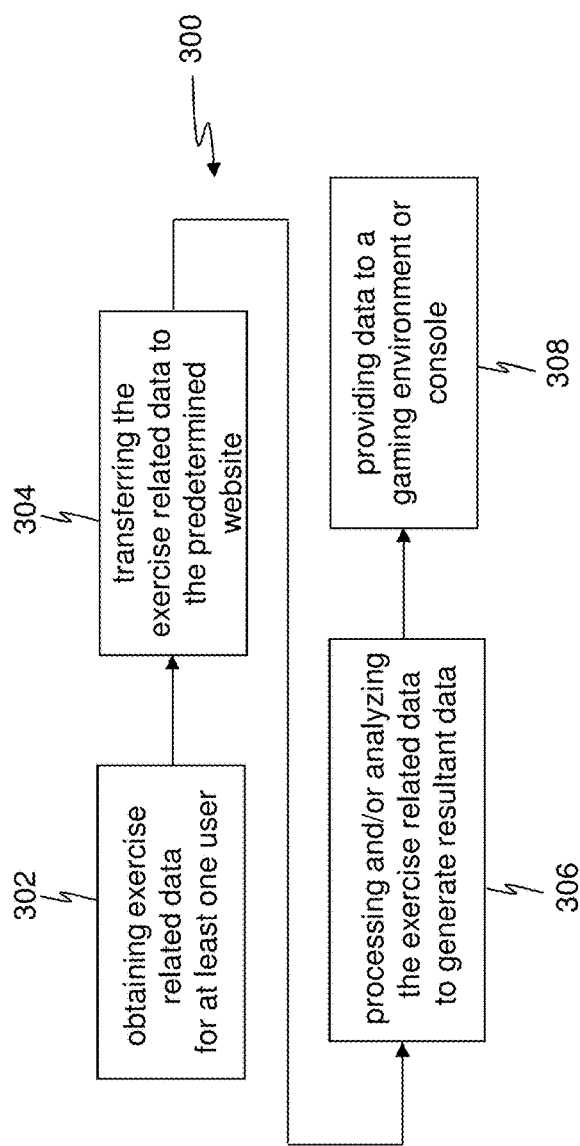
FIG. 4 is a block diagram illustrating a second embodiment of the method of the present invention.
Figure 5A:
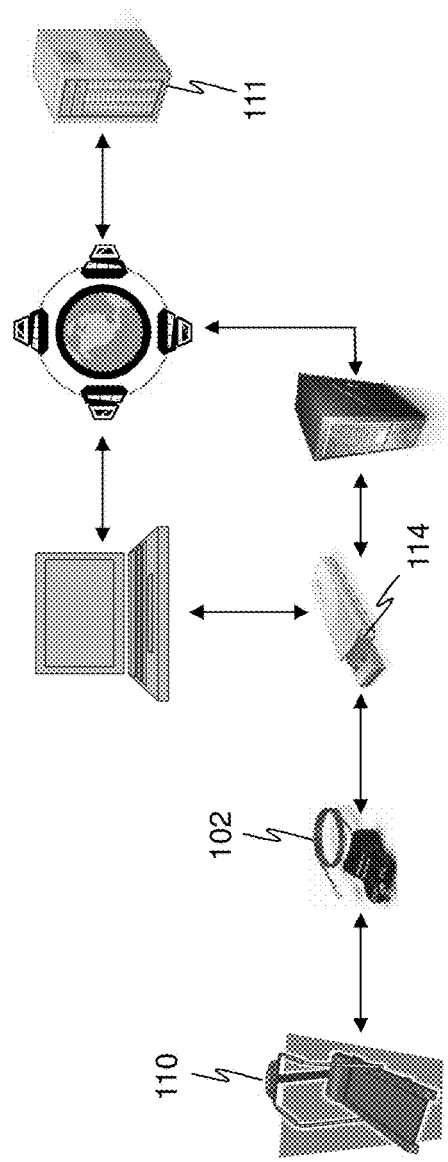
FIG. 5A is a block diagram illustrating the interaction of the system of FIG. 1, in accordance with the method of FIG. 4.
Figure 5B:
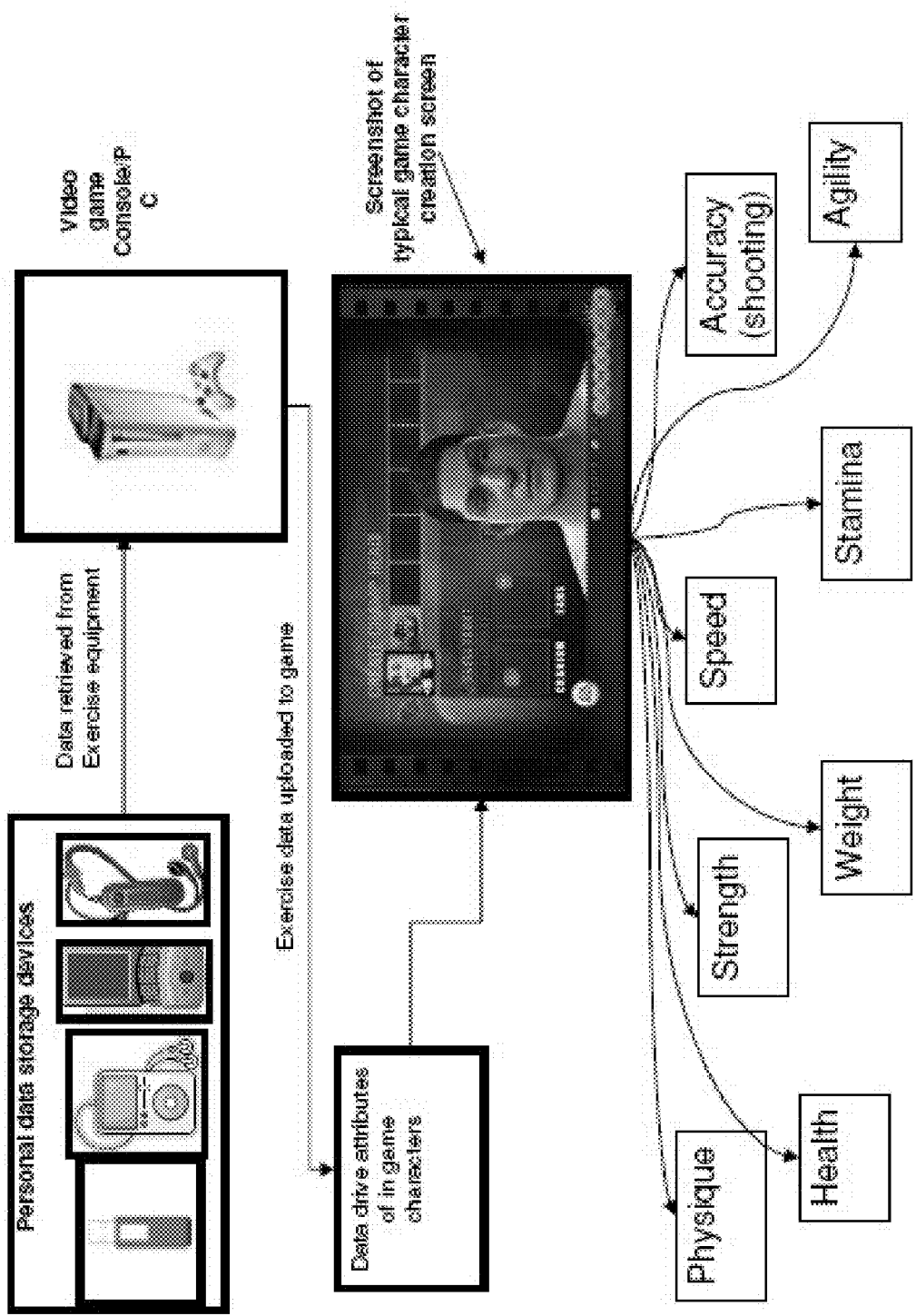
FIG. 5B is a functional block diagram illustrating the interaction of the system of FIG. 1, in accordance with the method of FIG. 4.

Referring to FIG. 4, a block diagram illustrating a second embodiment of a method 300 for processing exercise related information is shown, wherein the method 300 includes obtaining exercise related data for at least one user, as shown in operational block 302. The exercise related data may then be transferred to the predetermined website, as shown in operational block 304. The exercise related data may then be processed and/or analyzed to generate resultant data, as shown in operational block 306. This exercise related data and resultant data may then be introduced to a gaming environment, such as a PC game or an online gaming provider, where the physical attributes of the user can be carried over to the virtual character in the game, as shown in operational block 308 and as discussed further hereinafter. Referring to FIGS. 5A and 5B, block diagrams illustrating one embodiment of the interconnectivity between the user, the exercise device 110 and the gaming environment are shown.

In accordance with the present invention, the obtained exercise related data and/or resultant data may be used to augment or individualize a character in a gaming environment involving the user as described hereinafter. In this case, the website may provide the user (or interact with a separate entity to provide the user) with a gaming environment and model the characteristics of player in the gaming environment using the raw exercise related data and/or resultant data. For example, a virtual character within the game may have the same physical limitations or strengths as the user, such as height, weight, athletic ability and health problems. Similarly, the gaming environment itself may also be modeled in response to the raw exercise related data and/or resultant data. For example, if the user is not proficient at running, the gaming environment may include a lot of running. It is contemplated that this feature may also be ported over to personal gaming devices or virtual competitions sponsored by the website.

Accordingly, a video game such as a role playing game, sports game, fighting game, shooter/action game, etc, may use the raw exercise data and/or resultant data to drive the attributes of a character and/or environment created inside a 'game world' (i.e. cyberspace). For example, in one embodiment a user may connect to the gaming environment via a computer or gaming device (i.e. Playstation®, Gameboy®, X-Box®) and see their personal exercise affect the attributes (physical and/or performance) of their video game character in the 'game world'. Accordingly, as the conditioning of the user increases or decreases, the conditioning of the video game character would similarly increase or decrease. This would also provide another motivating factor for the user to continue exercising by giving the user a competitive advantage against other players or against computer controlled opponents.

Figure 6:
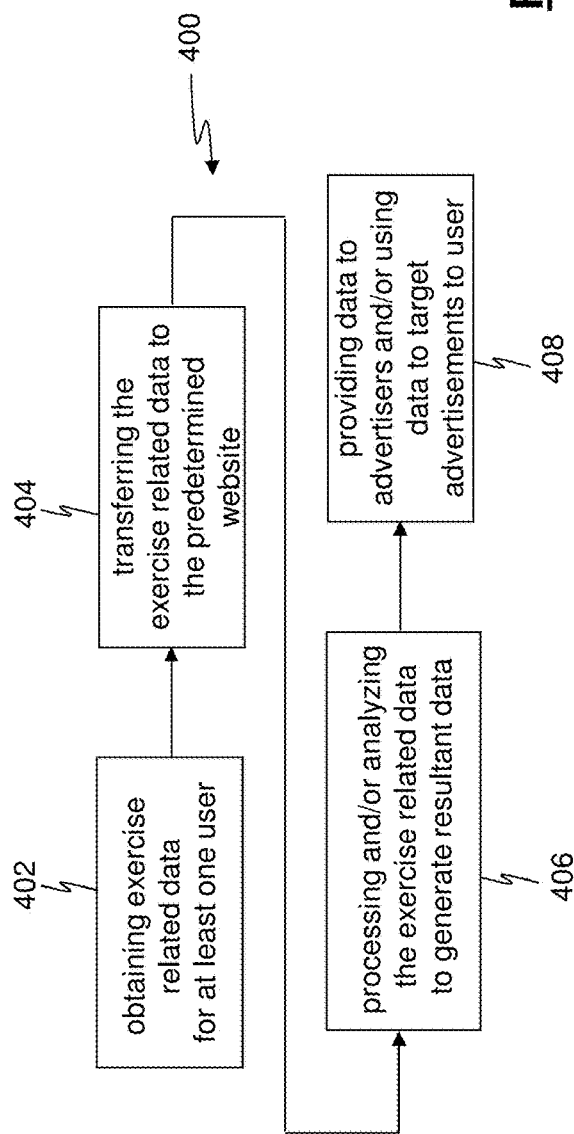
FIG. 6 is a block diagram illustrating a third embodiment of the method of the present invention.
Figure 7:
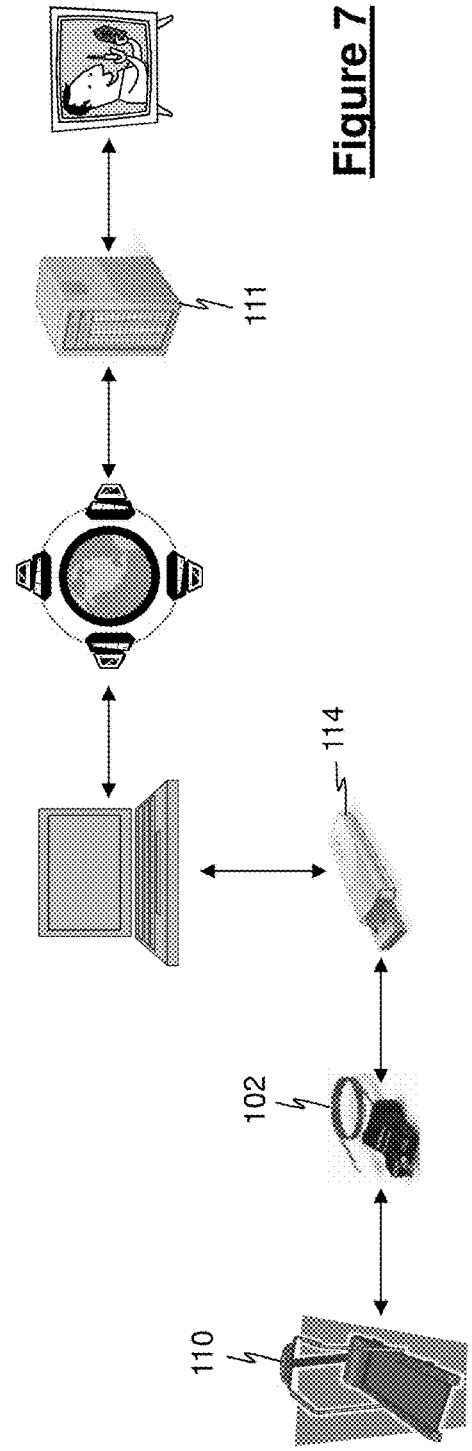
FIG. 7 is a block diagram illustrating the interaction of the system of FIG. 1, in accordance with the method of FIG. 6.

Referring to FIG. 6, a block diagram illustrating a third embodiment of a method 400 for processing exercise related information is shown, wherein the method 400 includes obtaining exercise related data for at least one user, as shown in operational block 402. The exercise related data may then be transferred to the predetermined website, as shown in operational block 404. The exercise related data may then be processed and/or analyzed to generate resultant data, as shown in operational block 406. This exercise related data and resultant data may then be provided to advertisers and/or used to target specific advertisements to the user, as shown in operational block 408 and as discussed further hereinafter. Referring to FIG. 7, a block diagram illustrating one embodiment of the interconnectivity between the user, the exercise device 110 and the gaming environment is shown.

In accordance with the present invention, the method 400 disclosed herein may allow for advertisements to be tailored to a registered user's personal profile information, workout regime or health conditions. For example, a 35 year old male in good physical condition may receive advertisements for golfing, running and waterskiing, while a 23 year old male in good physical condition may receive advertisements for mountain bikes and rollerblades. Additionally, a 40 year old male in moderate to poor physical condition may receive advertisements for health related products targeted for his age, social class and/or education. Since the advertisements are geared towards the information in the user profile, this provides an excellent opportunity for companies to target the advertisements of their goods and services to specific markets in various industries. Moreover, the website may provide a section where certified personal trainers and other professionals can interact with users to discuss topics, answer questions and offer suggestions to users on how to safely and effectively exercise and diet. Similarly, the website may also provide a section where certified personal trainers and other professionals can interact with other trainers/professionals to discuss topics, answer questions or get advice.

Figure 8:
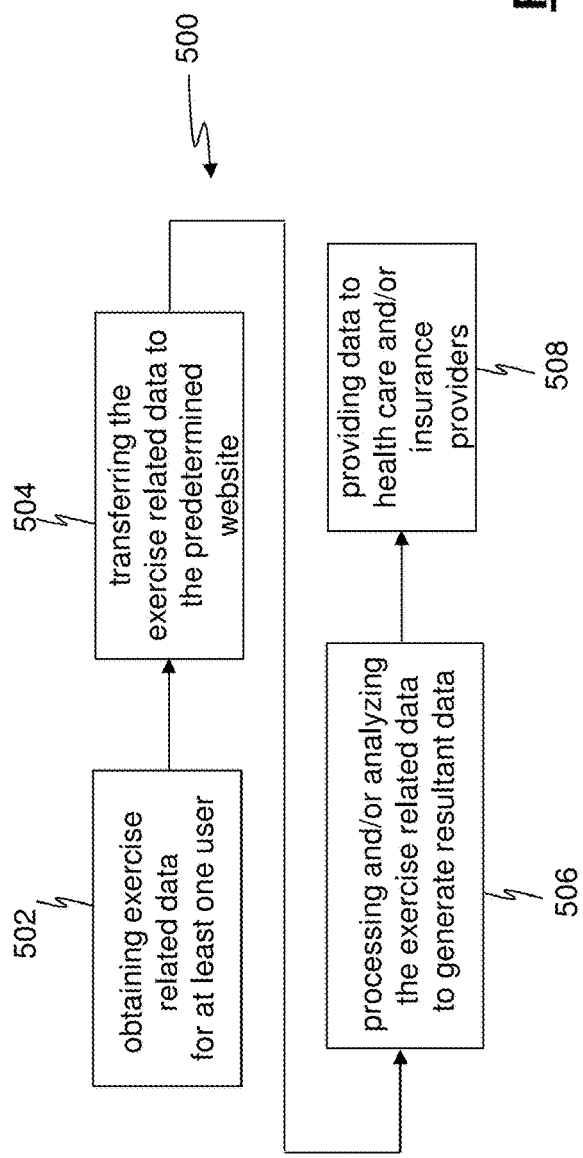
FIG. 8 is a block diagram illustrating a fourth embodiment of the method of the present invention.
Figure 9:
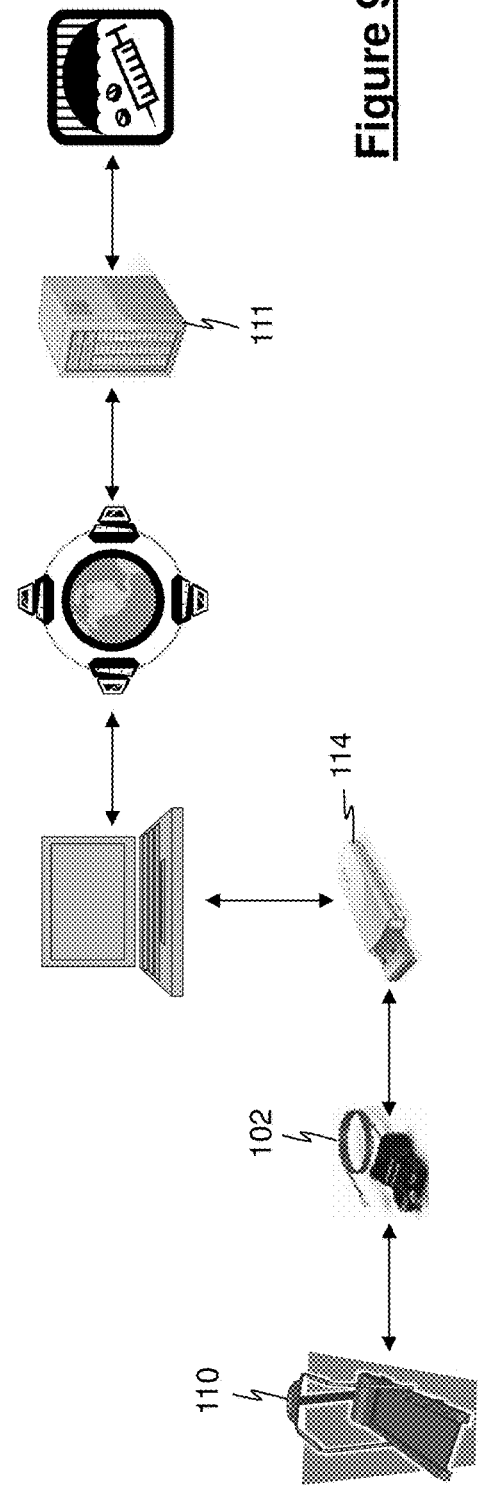
FIG. 9 is a block diagram illustrating the interaction of the system of FIG. 1, in accordance with the method of FIG. 8.

Referring to FIG. 8, a block diagram illustrating a fourth embodiment of a method 500 for processing exercise related information is shown, wherein the method 500 includes obtaining exercise related data for at least one user, as shown in operational block 502. The exercise related data may then be transferred to the predetermined website, as shown in operational block 504. The exercise related data may then be processed and/or analyzed to generate resultant data, as shown in operational block 506. This resultant data may then be used by an insurance provider to monitor the exercise habits, exercise performance, health status and/or exercise regime of a user insured by or applying for insurance by the insurance provider, as shown in operational block 508 and as discussed further hereinafter. Referring to FIG. 9, a block diagram illustrating one embodiment of the interconnectivity between the user, the exercise device 110 and the insurance provider is shown.

In accordance with the present invention, it is contemplated that the system of the present invention may make selected information about a user available to the user's health care and/or insurance provider as proof to the insurer that the user is indeed exercising and of the overall physical conditioning of the user. Accordingly, this system may be used by the health care and insurance industry, (for example health insurance providers) as a replacement for the honor system when tracking the exercise history of individuals. This may allow insurers the ability to verify that the insured is actually exercising on a consistent basis and that the insured is actually following a prescribed exercise regimen. Furthermore, this system may also provide proof that the insured is maintaining a health club membership, showing the frequency and level of effort the insured is demonstrating. The insurer may then use this information as a basis (at least partially) for assessing the insurance risk level and thus determining the premiums of the insured. For example, some companies and health care providers have implemented health incentive plans that are honor driven and that require employees to manually enter exercise data into a database. These providers may offer cash incentives in the form of monetary contributions deposited into the employees health/flexible spending accounts. The present invention can be used to help prevent fraud by providing a system and method which results in user and exercise data having a high degree of confidence and integrity.

As described above, the methods and embodiments described hereinabove and in the several figures may be embodied in the form of computer-implemented processes and apparatuses for practicing those processes. The methods and embodiments described hereinabove and in the several figures may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) may be updated to implement the invention. The methods and embodiments described hereinabove and in the several figures may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments may configure the microprocessor to create specific logic circuits. It should be further appreciated that the methods and embodiments described hereinabove may also be practiced, in whole or in part, via any device suitable to the desired end purpose, such as a computer, iPod, MP3 Player, a PDA, a Pocket PC and/or a Cell phone with connection capability.

It should be appreciated that although the device used to retrieve exercise information is discussed herein as a portable USB flash drive 114, the device used to retrieve exercise information may be any device suitable to the desired end purpose, such as MP3 player type devices, iPods, USB flash drives, Blackberrys, Pocket PCs, cell phones and any other type of device capable of storing data. It should also be appreciated that the device used to retrieve exercise information may further include wireless capabilities so that the user may access the website and upload exercise information via the wireless device. Moreover, the docking station 102 may include embedded software, firmware, and other drivers that have the ability to communicate with any compatible exercise fitness machine, such as a cardio fitness machine that is CSAFE compatible. Furthermore, although this invention is described herein as using the CSAFE protocol commands to capture pertinent workout data and transfer that data to the USB flash drive, any protocol command structure suitable to the desired end purpose may be used.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another. An apparatus and method for processing exercise information is provided, wherein the method includes obtaining exercise information, processing exercise information responsive to predetermined goals to generate resultant information and displaying the resultant information.

What is claimed is:

1. A biological monitoring device comprising:
  at least one sensor, included within the biological monitoring device, configured to obtain heart rate data associated with a person wearing the biological monitoring device;
  at least one processor in signal communication with the at least one sensor;

communication circuitry configured for bi-directional wireless communication with a external bio-metrically secure remote processing mobile device;

memory, included within the biological monitoring device, associated with one or more of the at least one processor and configured to store software instructions, which, when executed by the one or more of the at least one processor, cause the one or more of the at least one processor to perform operations comprising;

i. Establish, via the biological monitoring device processor, a bi-directional wireless communication link with the external bio-metrically secure remote processing mobile device;

ii. Obtain, via the biological monitoring device processor from the external bio-metrically secure remote processing mobile device, biological monitoring device configuration information;

iii. Obtain data, via the biological monitoring device processor, from the at least one sensor included within the biological monitoring device on at least one of an active or passive basis;

iv. Generate, via the at least one biological monitoring device processor, heart rate data responsive to the obtained sensor data;

v. Process, via the biological monitoring device processor, the heart rate data, wherein the processing of the heart rate data includes analyzing the heart rate data to detect at least one of an irregular heart rate, an abnormal heart rate, and an irregular heart rhythm;

vi. Generate, via the at least one biological monitoring device processor, resultant data based on the processing of at least one of the heartrate data, the irregular heart rate, the abnormal heart rate, and the irregular heart rhythm wherein the generated resultant data is at least one of a notification associated with a health condition of the person wearing the biological monitoring device and heart rate profile data of the person wearing the biological monitoring device;

vii. Display, via the biological monitoring device display, at least one of the generated resultant data and the processed heart rate data;

viii. Store, via the biological monitoring device memory, at least one of the heart rate data, the processed heart rate data, and the generated resultant;

ix. Communicate, via the biological monitoring device wireless communication circuitry, at least one of the heart rate data, the processed heart rate data, and the generated resultant data to the external bio-metrically secure remote processing mobile device, wherein the biological monitoring device configuration information received from the external bio-metrically secure remote processing mobile device is used to control at least one of the functionality and display of the biological monitoring device.

2. The biological monitoring device of claim 1, wherein the biological monitoring device includes a heart rate monitor.

3. The biological monitoring device of claim 1, wherein the biological monitoring device has a display, and wherein the biological monitoring device is configured to display at least one of the generated resultant data and the processed heart rate data.

4. The biological monitoring device of claim 1, wherein the processing includes encrypting at least one of the heart rate data, the processed heart rate data, and the generated resultant data prior to communicating data to the external bio-metrically secure remote processing mobile device.

5. The biological monitoring device of claim 1, wherein actively obtaining the data from the at least one sensor is performed by the biological monitoring device software on at least one of a continuous or semi-continuous basis.

6. The biological monitoring device of claim 1, wherein passively obtaining the data from the sensor is based on the at least one processor of the biological monitoring device being initiated by at least one of an event associated with monitoring the heartrate data and a threshold level associated with monitoring the heart rate data.

7. The biological monitoring device of claim 6, wherein the event that initiates passive monitoring is associated with at least one of the detected irregular heart rate, the detected abnormal heart rate, and the detected irregular heart rhythm.

8. The biological monitoring device of claim 6, wherein the threshold level that initiates passive monitoring is associated with at least one of the detected irregular heart rate, the detected abnormal heart rate, and the detected irregular heart rhythm.

9. The biological monitoring device of claim 1, wherein the external bio-metrically secure remote processing mobile device is at least one of a smartphone device, a tablet device, a pocket PC device, a portable media player device, and a portable gaming device.

10. The biological monitoring device of claim 1, wherein the notification that is generated responsive to the processed heart rate data indicates at least one of a health status and heath condition of the person wearing the biological monitoring device.

11. The biological monitoring device of claim 10, wherein the health condition is at least one of an irregular heart rate, an abnormal heart rate, an irregular heart rhythm, COPD, and hypertension.

12. The biological monitoring device of claim 1, wherein the biological monitoring device includes a blood pressure monitor.

13. A system for recording and displaying heart rate information of a person using a biological monitoring device and a bio-metrically secure remote processing mobile device external from the biological monitoring device, the system comprising:

a. The biological monitoring device in bi-directional wireless communication with the bio-metrically secure remote processing mobile device, the biological monitoring device comprised of:

i. At least one sensor, included within the biological monitoring device, configured to obtain data associated with the heart rate of the person using the biological monitoring device;

ii. At least one processor in signal communication with the at least one sensor;

iii. Communication circuitry configured for bi-directional wireless communication with the bio-metrically secure remote processing mobile device;

iv. Memory, included within the biological monitoring device, associated with the one or more processors and configured to store software instructions, which, when executed by the one or more processors, cause the one or more processors to perform operations comprising;

Establish, via the at least one biological monitoring device processor, a bi-directional wireless communication link with the bio-metrically secure remote processing mobile device;

Obtain, via the at least one biological monitoring device processor from the bio-metrically secure remote processing device, biological monitoring device configuration information;

Obtain data, via the at least one biological monitoring device processor, from at least one sensor included within the biological monitoring device on at least one of an active or passive basis;

Generate, via the at least one biological monitoring device processor, heart rate data responsive to the obtained sensor data;

Process, via the at least one biological monitoring device processor, the heart rate data, wherein the processing of the heart rate data includes analyzing the heart rate data to detect at least one of an irregular heart rate, an abnormal heart rate, and an irregular heart rhythm;

Generate, via the at least one biological monitoring device processor, resultant data based on the processing of at least one of the heart rate data, the irregular heart rate, the abnormal heart rate, and the irregular heart rhythm wherein the generated resultant data is at least one of a notification associated with a health condition of the person wearing the biological monitoring device and heart rate profile data of the person wearing the biological monitoring device;

Store, via the biological monitoring device memory, at least one of the heart rate data, the processed heart rate data, and the generated resultant data in memory included within the biological monitoring device;

Communicate, via the at least one biological monitoring device wireless communication circuitry, at least one of the heart rate data, the processed heart rate data, and the generated resultant data to the bio-metrically secure processing mobile device b. The bio-metrically secure remote processing mobile device in bi-directional wireless communication with the biological monitoring device, wherein the bio-metrically secure remote processing mobile device is comprised of;

i. One or more processors included within the bio-metrically secure remote processing mobile device;

ii. A display included within the bio-metrically secure remote processing mobile device wherein the display is in electronic communication with at least one of the processors included within the bio-metrically secure remote processing mobile device;

iii. Communication circuitry configured for bi-directional wireless communication with the biological monitoring device;

iv. Memory, included within the bio-metrically secure remote processing mobile device, associated with the one or more processors and configured to store software instructions, which, when executed by the one or more processors, cause the one or more processors to perform operations comprising;

send, via the bio-metrically secure remote processing mobile device communication circuitry, biological monitoring device configuration information to the biological monitoring device;

obtain, via the at least one bio-metrically secure remote processing mobile device processor from the biological monitoring device memory, at least one of the heart rate data, the processed heart rate data, and the generated resultant data;

process, via the at least one bio-metrically secure remote processing mobile device processor, at least one of the heart rate data, the processed heart rate data, and the generated resultant data;

v. a bio-metric sensor, included within the bio-metrically secure remote processing mobile device, configured to obtain a bio-metric characteristic of the person wearing the biological monitoring device wherein the obtained bio-metric characteristic is stored within the memory of the bio-metrically secure remote processing mobile device, wherein the biological monitoring device configuration information received from the biometrically secure remote processing mobile device by the at least one biological monitoring device processor is used to control at least one of the functionality and display of the biological monitoring device.

14. The system of claim 13, wherein the bio-metrically secure remote processing mobile device is at least one of a smartphone device, a tablet device, a music player device, and a portable gaming device.

15. The system of claim 13, wherein the biological monitoring device has a display, and wherein the biological monitoring device is configured to display at least one of the heart rate data, the processed heart rate data, and the generated resultant data wherein displaying the heart rate data also includes displaying heart rate profile data in at least one of a graphical format and non-graphical format.

16. The system of claim 13, wherein the processing performed on the at least one biological monitoring device processor further includes encrypting at least one of the heart rate data, the processed heart rate data, and the generated resultant data prior to communicating data to the bio-metrically secure remote processing mobile device.

17. The system of claim 13, wherein actively obtaining the data by the at least one biological monitoring device processor from the at least one sensor included within the biological monitoring device is performed by the biological monitoring device software on at least one of a continuous or semi-continuous basis.

18. The system of claim 13, wherein passively obtaining the data by the at least one biological monitoring device processor from the at least one sensor included within the biological monitoring device is based on being initiated by an event associated with at least one of monitoring the heart rate data and a threshold level associated with monitoring the heart rate data.

19. The system of claim 13, wherein the bio-metrically secure remote processing mobile device is further configured to establish a second wireless communication link with a remote website database for transferring at least one of the heart rate data, the processed heart rate data, and the generated resultant data to the remote website database, wherein the bio-metrically secure remote processing mobile device software contains a pre-determined website identifier associated with the remote website database.

20. The system of claim 13, wherein the processing of the data received by the at least one bio-metrically secure remote processing mobile device processor includes at least one of generating a heart rate data output file, generating encrypted heart rate data, erasing the obtained heart rate data from a memory location within the bio-metrically secure remote processing mobile device, periodically writing the obtained data received from the biological monitoring device to a memory location within the bio-metrically secure remote processing mobile device, and further generating resultant data based on at least one of the obtained heart rate data and the obtained processed heart rate data wherein at least one of heart rate data, the processed heart rate data, and the generated resultant data can be used by at least one of a health insurance provider for determining monetary contributions into a health spending account, by a video game for modeling at least one of a gaming environment and a gaming character based on at least one of the heart rate data, processed heart rate data, and the resultant data, and further by a medical practitioner for diagnosing a health condition associated with the user of the bio-metrically secure remote processing device.

21. The system of claim 13, wherein the health condition detected by the biological monitoring device is at least one of an irregular heart rate, an abnormal heart rate, an irregular heart rhythm, COPD, and hypertension.

22. The system of claim 13, wherein the biological monitoring device includes a blood pressure monitor.

* * * * *

UNITED STATES PATENT AND TRADEMARK OFFICE
CERTIFICATE OF CORRECTION

PATENT NO. : 11,252,235 B2
APPLICATION NO. : 16/570424
DATED : February 15, 2022
INVENTOR(S) : Sean McKirdy and Robert Nutini It is certified that error appears in the above-identified patent and that said Letters Patent is hereby corrected as shown below:

In the Specification

Column 1, Line 7, (Under the section titled: "CROSS-REFERENCE TO RELATED PATENT APPLICATIONS) cancel the text beginning with "The present application ..." and ending "... herein in their entirety" in Column 1, Line 15, and insert the following:
-- The present application is a continuation application claiming priority to co-pending U.S. Non-Provisional Patent Application Ser. No. 14/203,648, filed on March 11, 2014,
 wherein U.S. Non-Provisional Patent Application Serial No. 14/203,648 is a continuation claiming priority to co-pending U.S. Non-Provisional Patent Application Serial No. 13/350,790, filed on January 15, 2012 (now U.S. Patent 8,915,823, issued on December 23, 2014),
 wherein U.S. Non-Provisional Patent Application Serial No. 13/350,790 is a division claiming priority to co-pending U.S. Non-Provisional Patent Application Ser. No. 11/998,766, filed on November 30, 2007 (now U.S. Patent 8,118,709, issued on February 21, 2012),
 wherein U.S. Non-Provisional Patent Application Serial No. 11/998,766 is a Non-Provisional Application claiming priority to co-pending U.S. Provisional Patent Application Ser. No. 60/872,203, filed on Dec. 1, 2006,
 the contents of all of which are incorporated by reference herein in their entirety. --

Signed and Sealed this
Fifteenth Day of August, 2023

Katherine Kelly Vidal
*Director of the United States Patent and Trademark Office*